United States Patent [19]
Sterzer et al.

[11] Patent Number: 5,992,419
[45] Date of Patent: Nov. 30, 1999

[54] METHOD EMPLOYING A TISSUE-HEATING BALLOON CATHETER TO PRODUCE A "BIOLOGICAL STENT" IN AN ORIFICE OR VESSEL OF A PATIENT'S BODY

[75] Inventors: Fred Sterzer, Lawrence Township; Daniel D. Mawhinney, Livingston, both of N.J.

[73] Assignee: MMTC, Inc., Princeton, N.J.

[21] Appl. No.: 09/137,230

[22] Filed: Aug. 20, 1998

[51] Int. Cl.$^6$ ..................................................... A61B 17/39
[52] U.S. Cl. .............................. 128/898; 606/31; 606/42; 607/101; 607/102; 607/105
[58] Field of Search .................................. 606/27, 28–31, 606/41, 42; 607/100–102, 115, 116, 154, 156; 604/21, 22, 114; 128/898

[56] References Cited

U.S. PATENT DOCUMENTS

| | | | |
|---|---|---|---|
| 5,007,437 | 4/1991 | Sterzer | 607/156 |
| 5,149,198 | 9/1992 | Sterzer | 374/139 |
| 5,234,004 | 8/1993 | Hascoet et al. | 607/116 |
| 5,330,518 | 7/1994 | Neilson et al. | 607/101 |
| 5,496,271 | 3/1996 | Burton et al. | 604/54 |
| 5,509,929 | 4/1996 | Hascoet et al. | 607/101 |
| 5,620,480 | 4/1997 | Rudie | 607/101 |
| 5,688,050 | 11/1997 | Sterzer et al. | 374/122 |
| 5,693,082 | 12/1997 | Warner et al. | 607/156 |

OTHER PUBLICATIONS

Sterzer, Fred, "Localized Heating . . . Balloon Catheters", New Frontiers in Medical Device Technology, pp. 105–120, 1995.

*Primary Examiner*—Michael Peffley
*Attorney, Agent, or Firm*—George J. Seligsohn

[57] ABSTRACT

Disclosed are three embodiments of a method for determining the formation of a "biological stent" for permanently maintaining the widened bore portion of the urethra of a male patient undergoing treatment for a disease of the prostate. In this treatment, the bore portion is first temporarily widened by squeezing pressure on urethral tissue thereof applied by an inflated balloon of a microwave balloon catheter inserted in the urethera and then microwave energy sufficient to form the "biological stent" is applied to the urethral tissue. The first embodiment involves noting an observable drop in the measured value of the inflation pressure inflating the balloon when the urethral tissue has been sufficiently heated to effect a noticeable drop in the elasticity of the irradiated urethral tissue. The second embodiment involves a noticeable observable change in the measured value of the reflected microwave power received by the microwave-transmitting antenna when the urethral tissue has been sufficiently heated to effect a noticeable change in the reflectivity of the irradiated urethral tissue. The third embodiment involves a noticeable observable change in the measured value of the transmitted microwave power received by a directional microwave-receiving antenna within a patient's rectum when the urethral tissue has been sufficiently heated to effect a noticeable change in the transmissivity of the irradiated urethral tissue.

26 Claims, 6 Drawing Sheets

METHOD EMPLOYING A TISSUE-HEATING BALLOON CATHETER TO PRODUCE A "BIOLOGICAL STENT" IN AN ORIFICE OR VESSEL OF A PATIENT'S BODY

BACKGROUND

1. Field of the Invention

The method of the present invention relates broadly to the use of a tissue-heating balloon catheter for permanently widening the bore of an orifice or vessel of a patient's body and, more particularly, to the preferred use of a microwave balloon catheter for permanently widening the bore of the urethra of a male patient suffering from a disease of the prostate (such as benign prostatic hypertrophy (BPH) or prostate cancer) which results in an enlarged prostate that causes the bore of the urethra be narrowed.

2. Description of the Prior Art

Incorporated herein by reference is U.S. Pat. No. 5,007, 437, entitled "Catheters for Treating Prostate Disease," which issued to Fred Sterzer on Apr. 16, 1991 and is assigned to the same assignee as the present application. Briefly, U.S. Pat. No. 5,007,437 discloses that applying squeezing pressure to a diseased prostate, by means of a urethral and/or rectal catheter incorporating an inflatable prostate balloon, to compress the prostate while it is being irradiated from a microwave antenna, increases the therapeutic temperature to which the prostate tissue more distal to the microwave antenna can be heated without heating any non-prostate tissue beyond a maximum safe temperature, and reduces the temperature differential between the heated more distal and more proximate prostate tissue from the microwave antenna.

Further, reference is made to Chapter Four (pages 105–120) of the publication *New Frontiers in Medical Device Technology*, edited by Rosen et al. and published by John Wiley & Sons, Inc. in 1995. This Chapter Four, which is authored by Fred Sterzer and is entitled "Localized Heating of Deep-Seated Tissues Using Microwave Balloon Catheters," discloses, on pages 110 and 111, in vitro experiments which show that simultaneous ballooning and microwave heating to a 45° C. of an animal vessel resulted in the vessel becoming stiff with a wide-open lumen, becoming, in effect, a "biological stent." Further, Chapter Four discloses, on page 117, that the temperatures produced inside the treated prostate can be non-invasively measured with a microwave radiometer and, on page 118, that with microwave balloon catheters it is possible to produce high therapeutic temperatures throughout the prostate gland without causing burning of tissues and to produce "biological stents" in the urethra in a single treatment session. In this regard, reference is made to U.S. Pat. No. 5,149,198, which issued to Sterzer on Sep. 22, 1992, and U.S. Pat. No. 5,688,050, which issued to Sterzer et al. on Nov. 18, 1997, which patents are directed to radiometers which may be used for measuring the temperature of a patient's body tissue. Finally, Chapter Four concludes, on pages 118 and 119, that potential applications for microwave balloon catheters include the production of "biological stents" in partially obstructed vessels or in the urethra.

There is a need for a safe and effective method for realizing the possibility of the aforesaid potential application of producing "biological stents" in partially obstructed vessels or in the urethra.

SUMMARY OF THE INVENTION

The present invention is directed to a safe and effective method for realizing the production of a "biological stent" in a partially obstructed vessel or in an orifice, such as the urethra, of a patient.

More specifically, as in the prior art, the method of the present invention includes the steps of (1) longitudinally situating a deflated balloon of a balloon catheter in the narrowed bore portion of an orifice or vessel of a patient, (2) inflating the balloon to apply sufficient squeezing pressure on tissue of the narrowed bore portion of the orifice or vessel to effect a certain amount of temporary widening of the narrowed bore portion of the orifice or vessel as long as the squeezing pressure is maintained, and (3) heating the narrowed bore portion of the tissue (preferably by employing a microwave generator having a microwave-transmitting antenna surrounded by the balloon) to irradiate the temporarily widened bore portion of the tissue with microwave energy). However, as an improvement to the prior art, the method of the present invention includes the further step (a) of measuring an observable value of an analog (such as the value of the pressure inflating the balloon or the value of reflected or received microwave power) of the value of a physical characteristic (such as the elasticity or, alternatively, the reflectivity or transmissivity to incident microwave energy) of the tissue of the narrowed bore portion of the orifice or vessel which significantly changes in value from a first value to a second value when a "biological stent" in the tissue of the narrowed bore portion of the orifice or vessel is formed in response to the orifice or vessel tissue having been sufficiently heated. In this manner, it is determined when the temporarily widened bore portion of the tissue of the narrowed bore portion of the orifice or vessel has been sufficiently heated to form a "biological stent" that is capable of maintaining the bore portion of the tissue of the orifice or vessel permanently widened after the balloon has been deflated and the squeezing pressure on the bore portion of the tissue of the narrowed bore portion of the orifice or vessel has been removed.

DESCRIPTION OF THE PREFERRED EMBODIMENTS

Figure 1:
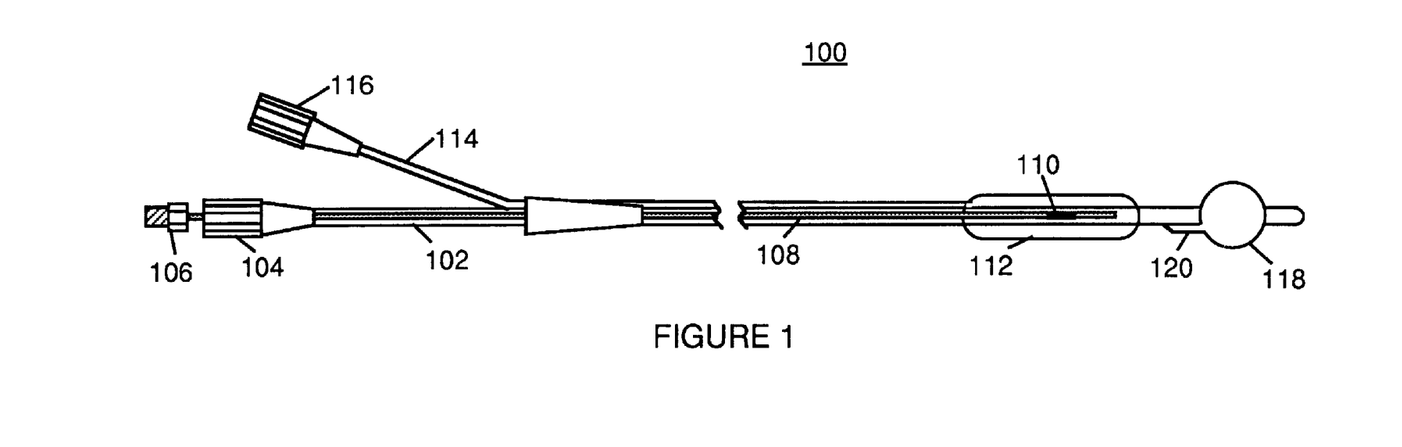
FIG. 1 is a diagrammatic showing of a microwave balloon catheter which may be employed, in accordance with the method of the present invention, for producing a "biological stent" in the urethral tissue of a male patient suffering from a disease of the prostate which results in an enlarged prostate that causes the bore of the urethra be narrowed.

Referring to FIG. 1, there is shown microwave balloon catheter 100 for use in treating a male patient suffering from a disease of the prostate which results in an enlarged prostate that causes the bore of the urethra be narrowed. Microwave balloon catheter 100 comprises first lumen 102 terminated at its left end by first port 104. Microwave energy connector 106, attachable to first port 104, includes microwave coupling cable 108 extending through lumen 102 for forwarding microwave energy to microwave antenna 110. Surrounding microwave antenna 110 is balloon 112, which may be inflated by a fluid (i.e., a liquid or a gas) supplied thereto through second lumen 114 terminated at its left end by second port 116. Because catheter 100 is to be inserted into the urethra of a male patient for use in treating his enlarged prostate, it also includes conventional Foley balloon 118 which may be inflated by a fluid supplied thereto through third lumen 120 (which is only partially shown in order to maintain clarity of the more significant structure of the drawing).

Figure 1A:
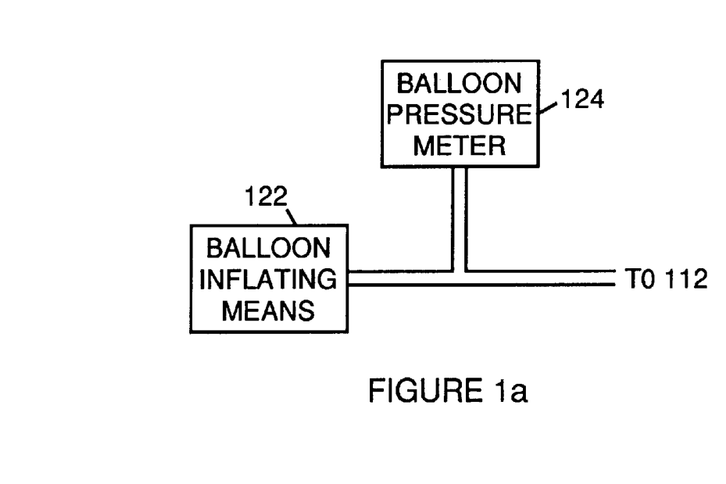
FIG. 1a is a functional block diagram of basic means for use in inflating the balloon of the microwave balloon catheter of FIG. 1 in the performance of a first preferred embodiment of the method of the present invention for producing the "biological stent" in the urethral tissue of a male patient suffering from a disease of the prostate which results in an enlarged prostate that causes the bore of the urethra be narrowed.

As functionally shown in FIG. 1a, balloon inflating means 122 coupled to second port 116 supplies a fluid under pressure to balloon 112 through second lumen 114. By way of alternative examples, balloon inflating means 122 may comprise a syringe or a pump that provides a continuous fluid flow with a controlled output restriction to create a back pressure. Balloon pressure meter 124 is used to continuously measure the fluid pressure value within balloon 112.

Balloon 112 comprises a thin film that is flexible and highly pliable (e.g., vinyl film), but is not highly elastic (e.g., natural or silicone rubber material). Therefore, balloon 112, when fully-inflated, will not tend to stretch to any appreciable extent when subjected to internal pressure. In this regard, balloon 112 is similar to an inflatable toy, which, in its deflated state, may be easily folded and/or pleated to have a relatively small cross-section. However, in its fully-inflated state, balloon 112 has a predetermined shape of a predetermined maximum size that has a relatively large maximum cross-section. An attempt to further inflate balloon 112 will not cause the predetermined maximum size to increase to any appreciable extent, but will only cause the internal pressure value to rise, since there is very little stretching of the thin film comprising balloon 112. If one were to substantially indent the thin film comprising balloon 112, the internal pressure value therein would be substantially increased and the total enclosed volume thereof would be substantially decreased.

Thus, there is a single-valued inverse relationship between the internal pressure value within balloon 112, as measured by balloon pressure meter 124, and the volume of a partially or fully inflated balloon 112. By experimentally calibrating and recording this inverse volume-pressure relationship for balloon 112, the pressure value measured by balloon pressure meter 124 can be used as a measure of the then-existing volume of a partially or fully inflated balloon 112.

Figure 1B:
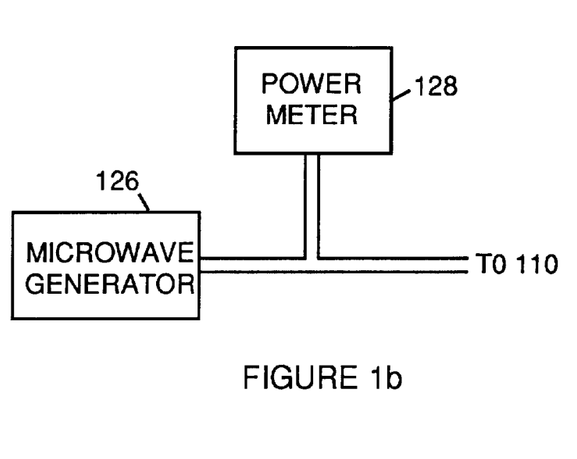
FIG. 1b is a functional block diagram of means for use in generating and then applying microwave energy to the microwave balloon catheter of FIG. 1 in the performance of the first embodiment of the method of the present invention for producing the "biological stent" in the urethral tissue of a male patient suffering from a disease of the prostate which results in an enlarged prostate that causes the bore of the urethra be narrowed.

As functionally shown in FIG. 1b, microwave energy from microwave generator 126 is forwarded to microwave antenna 110 through connector 106, first port 104 and microwave coupling cable 108. The power of the microwave energy forwarded to microwave antenna 110 may be continuously measured by power meter 128.

Figure 2:
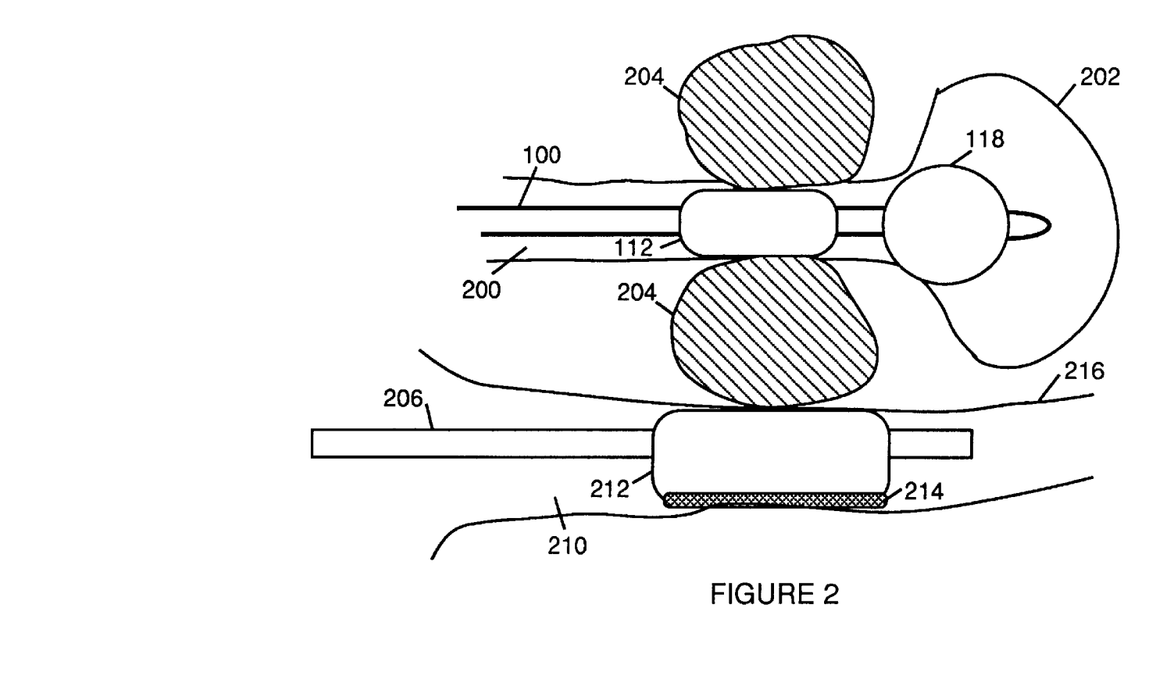
FIG. 2 is a diagrammatic showing of the relevant tissue of a male patient suffering from a disease of the prostate which results in an enlarged prostate that causes the bore of the urethra be narrowed who is undergoing a treatment employing the microwave balloon catheter of FIG. 1 for producing a "biological stent" in the urethral tissue of the male patient in accordance with the method of the present invention.

Referring now to FIG. 2, there is shown microwave balloon catheter 100 inserted in urethra 200 of a male patient undergoing a treatment for an enlarged prostate. As is conventional, inflated Foley balloon 118 is inserted into bladder 202 of the patient, Balloon 112 (which surrounds microwave antenna 110 not shown in FIG. 2) is longitudinally situated next to the urethral tissue which is in proximity to the patient's prostate 204. Further, a rectal probe 206 from temperature-measuring radiometer 208 (shown in FIG. 2a) is inserted the patient's rectum 210. As indicated in FIG. 2, rectal probe 206 comprises directional antenna 212, incorporating reflector 214, that is longitudinally situated in proximity to the patient's prostate 204 for receiving microwave or radio frequency energy radiated out through rectal tissue 216 of the patient's rectum 210 which is in contact with the patient's prostate 204.

As known, the increased volume of the prostate of a male patient suffering from an enlarged prostate causes the bore of the urethra in the vicinity of the prostate to be a narrowed. The method of the present invention for producing a "biological stent" for permanently widening the narrowed bore of the urethra of such a male patient is similar to the method disclosed in the aforesaid U.S. Pat. No. 5,007,437 only to the extent that both methods include the step of utilizing an inflated balloon (i.e., balloon 112) to apply sufficient squeezing pressure to the urethral tissue which is in proximity to the patient's prostate to cause the narrowed bore of the urethra to be widened while the pressure is being applied, and the step of irradiating the squeezed urethral tissue with microwave energy (i.e., microwave energy radiated from microwave antenna 110) while the pressure is being applied. However, of these two methods, only each of the following embodiments of the method of the present invention is directed to a safe and efficacious way of producing a "biological stent" for permanently widening the narrowed bore of the urethra.

In accordance with a first preferred embodiment of the method of the present invention, a urologist employs balloon inflating means 122 to partially inflate balloon 112 to a given squeezing pressure value (measured by balloon pressure means 124) which is sufficient to widen the narrowed diameter of the bore of urethra 200 to a selected value. However, this given squeezing pressure value is insufficient to inflate balloon 112 to its maximum volume. In accordance with a discovery of the present invention, it has been found that when the squeezed urethral tissue irradiated with microwave energy radiated from microwave antenna 110 is sufficiently heated, the pressure value measured by balloon pressure means 124 noticeably drops from the given value to another lower value. This drop in pressure value is due to a material permanent drop in the value of the elasticity of the squeezed urethral tissue. More specifically, the urethral tissue initially has a relatively high value of elasticity. Therefore, the initial urethral tissue, when squeezed by partially-inflated balloon 112, reacts by applying a relatively high value of back pressure to balloon 112. However, the lower value of elasticity of the urethral tissue after being sufficiently heated results in a noticeable lowering of the value of back pressure applied to squeezed balloon 112. This permits the volume of partially-inflated balloon 112 to expand, thereby noticeably lowering the value of the pressure within balloon 112, as measured by balloon pressure means 124. Thus, the value of the pressure measured by balloon pressure means 124 is an analog of the value of the elasticity of the squeezed urethral tissue. It has also been found that this drop in elasticity value, which occurs at a tissue temperature somewhere in a range of 45° C. to 50° C., is indicative of urethral tissue changes that result in the changed urethral tissue forming a "biological stent", wherein the changed urethral tissue becomes stiff and results in the minimum diameter of the bore of urethra 200 being maintained at a widened value close to the aforesaid selected value after balloon 112 has been deflated. Thus, a urologist may use an observed noticeable drop in the measured pressure value by balloon pressure meter 124 of the fluid inflating balloon 112 as an indicator that such a "biological stent" has been formed. Preferably, the fluid inflating balloon 112 comprises a material, such as air, exhibiting a low loss factor to irradiating microwave energy. The use of such a material exhibiting a low loss factor insures that substantially all of the irradiating microwave energy is absorbed by the urethral tissue, rather than a significant amount of the irradiating microwave energy being absorbed by the fluid inflating balloon 112.

Since the changed urethral tissue forming the "biological stent" is likely to exert some (although a significantly lower value) back pressure on inflated balloon 112 at the time that the "biological stent" is formed, the minimum diameter size of the bore of urethra 200 is likely to be somewhat smaller than the aforesaid selected value after balloon 112 has been deflated.

In order to determine the actual minimum diameter size of the bore of urethra 200 after balloon 112 has been deflated, balloon 112 may be slowly reinflated by the urologist using a metered amount of a liquid inflating fluid to the point at which the flexible and pliant thin film material of which balloon 112 is made to just conform to the "biological stent" tissue surface of urethra 200. At this point, the pressure value measured by balloon pressure meter 124 and monitored by the urologist will just start to rise due to the occurrence of some back pressure of the "biological stent" tissue on balloon 112. The metered amount of the liquid inflating fluid, observed by the urologist, at which this rise start occurs is indicative of the volume and, hence, the actual minimum diameter size of the bore of urethra 200. If this actual minimum diameter size of the bore of urethra 200 is still smaller than desired, a further increase in minimum diameter size can be obtained by repeating the aforesaid process employing balloon inflating means 122 to provide increased inflation pressure value for balloon 112 (as measured by balloon pressure meter 124), increased microwave power from microwave generator 126 (as measured by power meter 128) and/or increased treatment time for irradiating (and, hence, heating) the patient's urethral tissue with microwave energy from microwave generator 126.

Figure 2A:
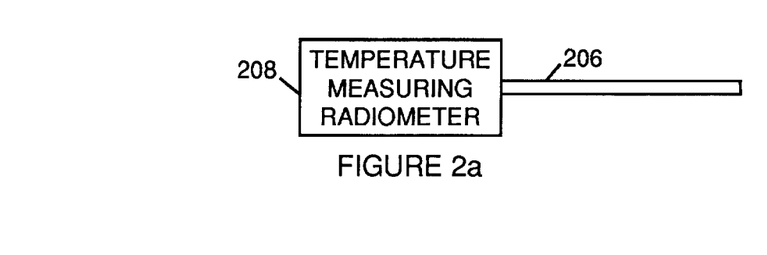
FIG. 2a is a functional block diagram of means including a radiometer for use in measuring the temperature of the rectal tissue shown in FIG. 2.

It is apparent that a "biological stent" is produced by a permanent beneficial change in the pressure and heat treated urethral tissue. However, overheating of urethral, prostate and/or rectal tissue irradiated by microwave energy causes a permanent detrimental change in such tissue. Rectal tissue is particularly subject to such permanent detrimental change if heated above a maximum safe temperature. In order to make sure that the above-described process for producing a "biological stent" does not inadvertently result in heating irradiated rectal tissue above this maximum safe temperature, probe 206 of temperature-measuring radiometer 208 is inserted in the rectum of the male patient suffering from an enlarged prostate who is being treated, as shown in FIGS. 2 and 2*a*. This permits the urologist to monitor the temperature measured by radiometer 208, and control microwave generator 126 to lower the generated microwave energy (or, alternatively, turn generator 126 off) if it appears likely that the monitored temperature become excessive. In this regard, radiometer 208 may have an alarm incorporated therein to alert the urologist to the fact that the temperature of the irradiated rectal tissue is about to reach or, at least, has reached the maximum safe temperature.

The permanent beneficial change in the pressure and heat treated urethral tissue that results in the production of a "biological stent" is not limited to the noticeable but permanent drop in the elasticity value of the urethral tissue, which noticeable drop is used by the above-described first preferred embodiment of the method of the present invention to indicate that a "biological stent" has been formed. Another permanent beneficial change which may be used to indicate that a "biological stent" has been formed is a noticeable but permanent change in the microwave properties of the treated urethral tissue that results in consequent noticeable but permanent changes in the microwave reflectivity value and microwave transmissivity of the treated urethral tissue. One cause, among others, for these changes in microwave properties and consequent reflectivity and transmissivity values is a change in the value of the dielectric constant of the treated urethral tissue (which results in a power-matching change) that affects (1) the amount of power reflected back to microwave generator 126 (through microwave antenna 110, microwave coupling cable 108 and microwave energy connector 106) from urethral tissue of urethra 200 irradiated with incident microwaves, and (2) the amount of the incident microwave power which reaches rectal probe 206 after being transmitted through both the urethral and rectal tissues of the patient. Thus, in accordance with a second preferred embodiment of the method of the present invention shown in FIG. 3*a*, noticeable changes in the relative amount of reflected microwave power with respect to transmitted microwave power (i.e., the ratio of reflected microwave power to transmitted microwave power) may be employed as an indicator that a "biological stent" has been formed. Also, in accordance with a third preferred embodiment of the method of the present invention shown in FIG. 3*b*, noticeable changes in the relative amount of microwave power received by rectal probe 206 with respect to transmitted microwave power (i.e., the ratio of microwave power received by rectal probe 206 to transmitted microwave power) may be employed as an indicator that a "biological stent" has been formed.

Figure 3A:
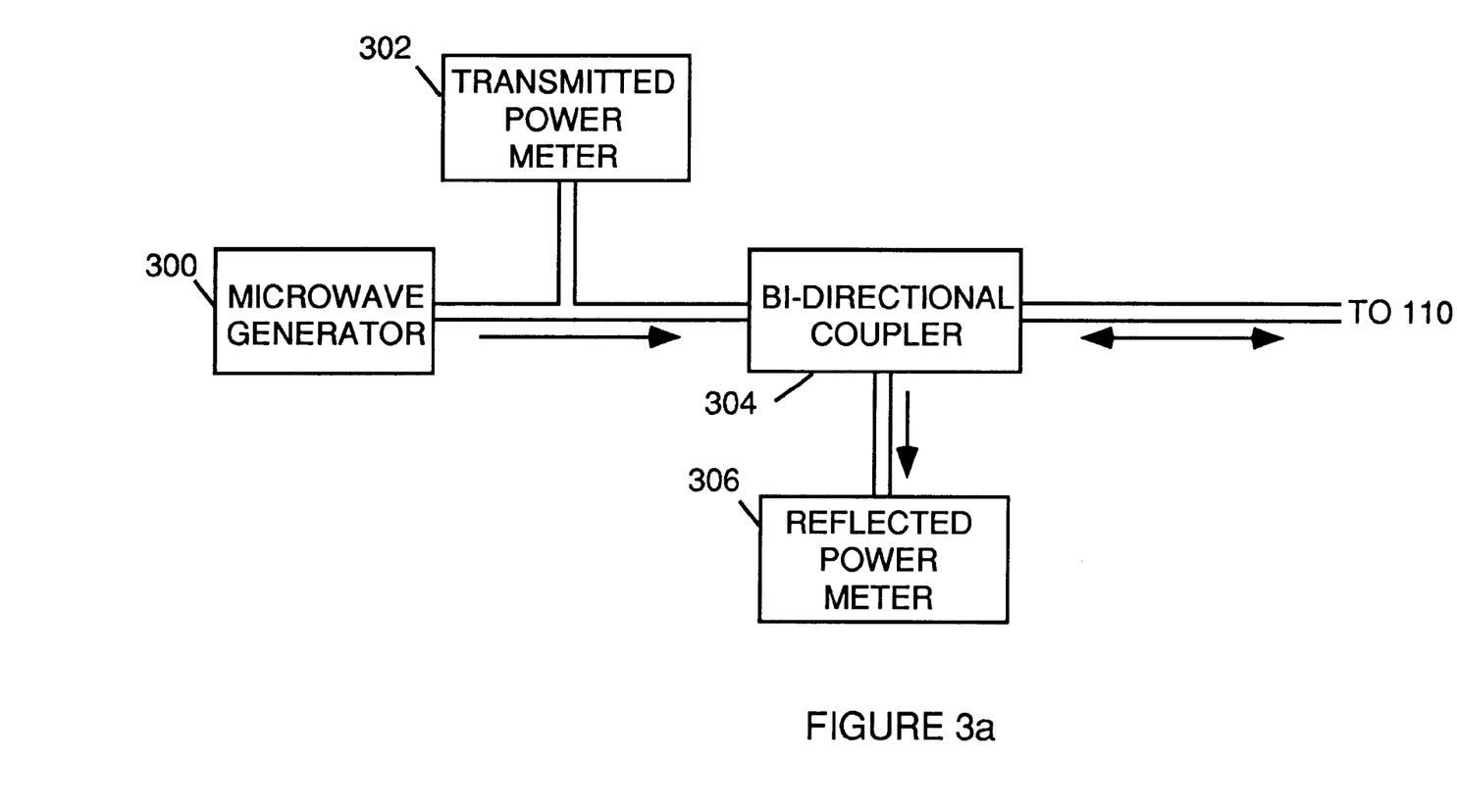
FIG. 3a is a functional block diagram of means for use in performing a second preferred embodiment of the method of the present invention for producing the "biological stent" in the urethral tissue of a male patient suffering from a disease of the prostate which results in an enlarged prostate that causes the bore of the urethra be narrowed.

As shown by the arrows in FIG. 3a, transmitted microwave power from microwave generator 300, which is continuously measured by transmitted microwave power meter 302, is forwarded through bi-directional coupler 304 to microwave antenna 110, while the reflected microwave power continuously received by microwave antenna 110 is fed back through bi-directional coupler 304 to reflected microwave power meter 306. Thus, the value measured by reflected microwave power meter 306 is an analog of the value of the reflectivity of the heated urethral tissue. A urologist may employ an observed noticeable change in the value of the microwave power measured by reflected microwave power meter 306 as an indication that a "biological stent" has been formed.

Figure 3B:
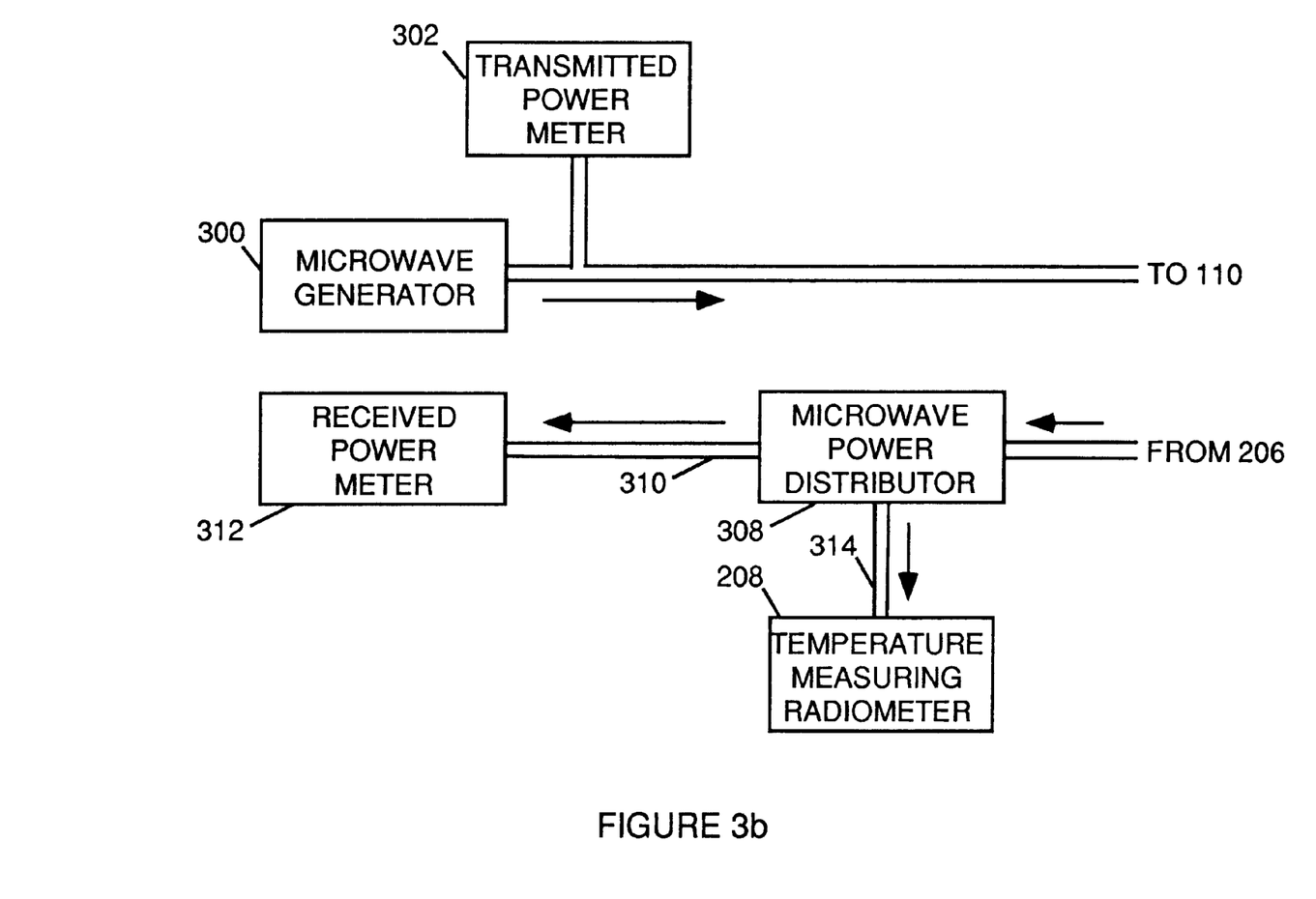
FIG. 3b is a functional block diagram of means for use in performing a third preferred embodiment of the method of the present invention for producing the "biological stent" in the urethral tissue of a male patient suffering from a disease of the prostate which results in an enlarged prostate that causes the bore of the urethra be narrowed.

As shown by the arrows in FIG. 3b, transmitted microwave power from microwave generator 300, which is continuously measured by transmitted microwave power meter 302, is forwarded directly to microwave antenna 110, while the microwave power from microwave antenna 110, which is transmitted through the patient's urethral and rectal tissue, is continuously received by directional antenna 212 (shown in FIG. 2) and then fed back through rectal probe 206 as an input to microwave power distributor 308. Microwave power distributor 308 can comprise (1) a manually-operated switch for alternatively forwarding the microwave power at the input to microwave power distributor 308 to either first output 310 (which is coupled to received power meter 312) or second output 314 (which is coupled to temperature measuring radiometer 208) of microwave power distributor 308, (2) a periodically-operated switch for forwarding the microwave power at the input to microwave power distributor 308 to first output 310 thereof during a first portion and to second output 314 thereof during the remaining portion of each successive period of the periodically-operated switch, or (3) a bandsplit filter that forwards a first band of microwave frequencies at the input to microwave power distributor 308 (which first band includes the microwave frequency generated by microwave generator 300) to first output 310 thereof and forwards a second band of microwave frequencies at the input to microwave power distributor 308 (which second band includes the microwave frequencies indicative of the temperature of the patient's tissue to be measured by temperature measuring radiometer 208) to second output 310 thereof. Thus, the value measured by received microwave power meter 312 is an analog of the value of the transmissivity of the heated urethral tissue. A urologist may employ an observed noticeable change in the value of the microwave power measured by received microwave power meter 306 as an indication that a "biological stent" has been formed, while employing temperature measuring radiometer 208 to ensure that the heated urethral tissue never exceeds a maximum safe temperature.

Figure 3C:
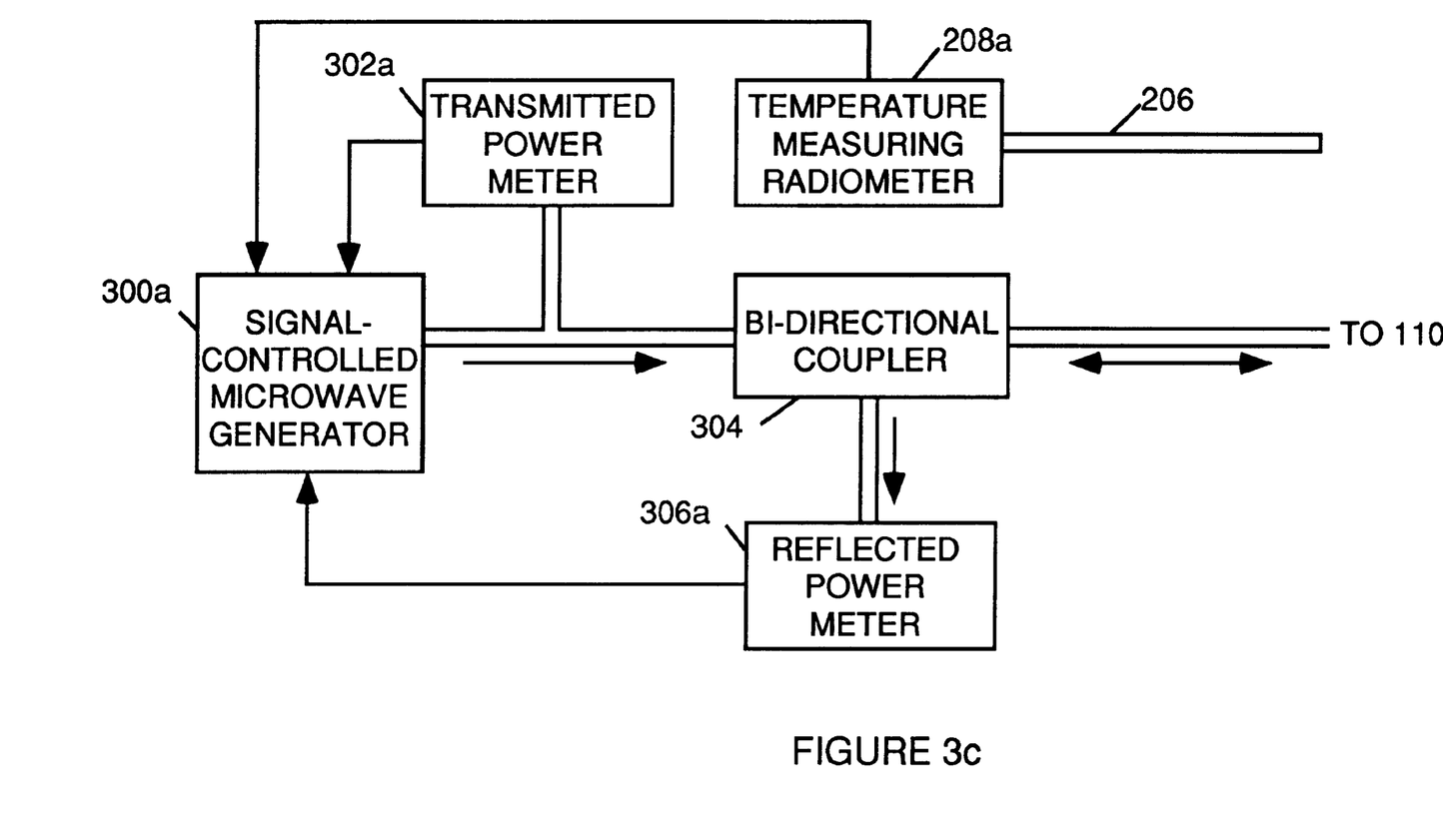
FIG. 3c is a functional block diagram of a modification of the means of FIG. 3a which permits a more automated performance of the second preferred embodiment of the method of the present invention for producing the "biological stent" in the urethral tissue a male patient suffering from a disease of the prostate which results in an enlarged prostate that causes the bore of the urethra be narrowed.

Further, as functionally shown in FIG. 3c, FIG. 3a may be modified to permit control of the microwave power output of microwave generator to be responsive to control signals fed back thereto. More specifically, microwave generator 300 of FIG. 3a is modified in FIG. 3c to provide signal-controlled microwave generator 300a; transmitted power meter 302 of FIG. 3a is modified in FIG. 3c to provide transmitted power meter 302a which feeds back a transmitted-power-indicating signal as a first control signal to signal-controlled microwave generator 300a; and reflected power meter 306 of FIG. 3a is modified in FIG. 3c to provide reflected power meter 306a which feeds back a reflected-power-indicating signal as a second control signal to signal-controlled microwave generator 300a. In addition, the structure functionally shown in FIG. 3a also includes temperature-measuring radiometer 208a coupled to rectal probe 206. Temperature-measuring radiometer 208a, which replaces temperature-measuring radiometer 208 of FIG. 2a, feeds back a third control signal to signal-controlled microwave generator 300a which is continuously indicative of the current temperature of the patient's rectal tissue.

Signal-controlled microwave generator 300a may include logic means responsive to the first and second control signals for determining the ratio of the reflected power value to the transmitted power value and means for causing the transmitted microwave power output from signal-controlled microwave generator 300a to be turned off in response to a noticeable change in the value of this ratio. Signal-controlled microwave generator 300a may also include means responsive to the third control signal for regulating the value of the microwave power output from signal-controlled microwave generator 300a in accordance with the value of the radiometer-measured temperature to insure that the temperature of the irradiated rectal tissue never exceeds a safe maximum temperature or, at least, causing the transmitted microwave power output from signal-controlled microwave generator 300a to be turned off in response to the temperature of the irradiated rectal tissue reaching this safe maximum temperature.

Figure 3D:
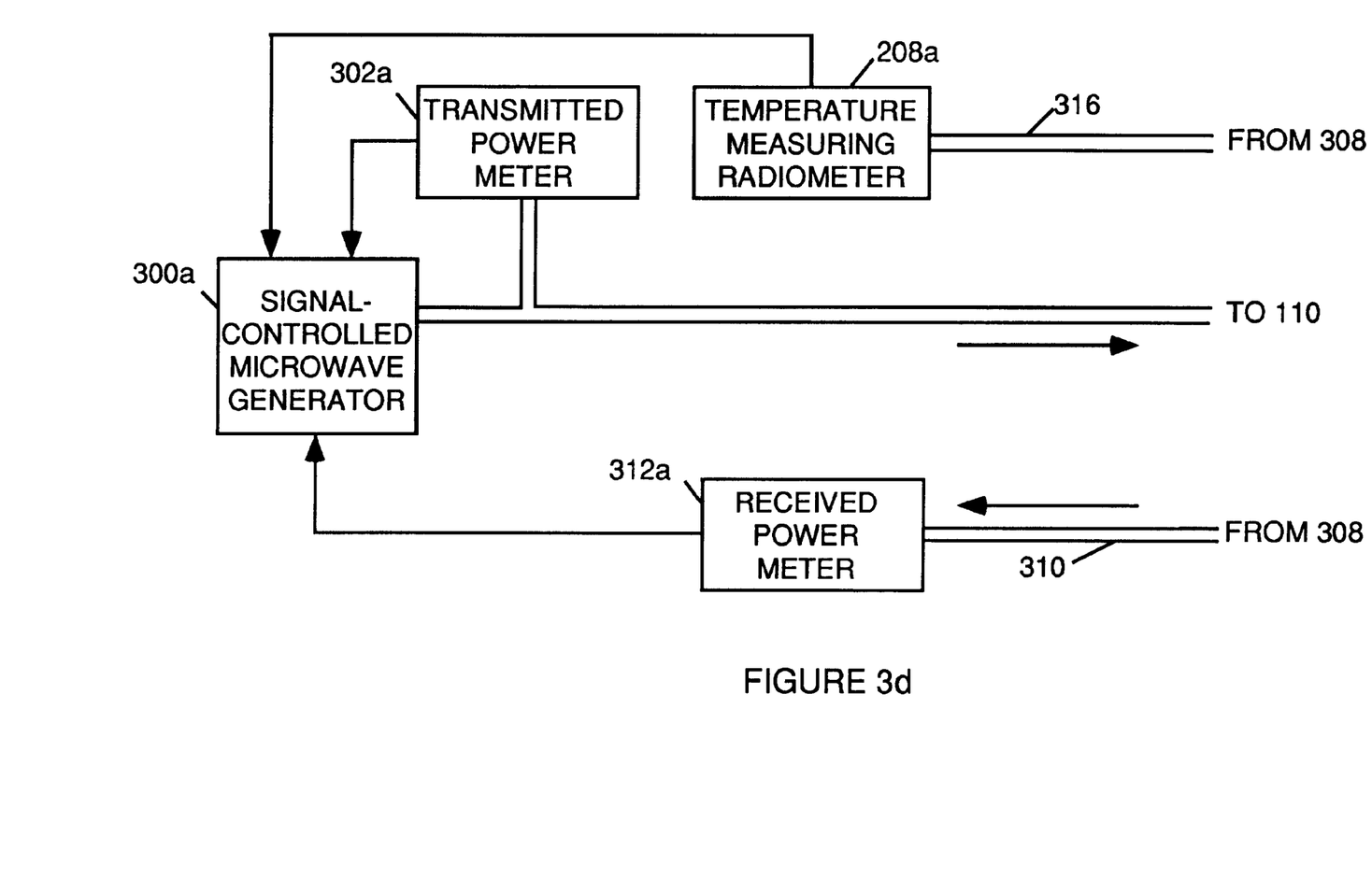
FIG. 3d is a functional block diagram of a modification of the means of FIG. 3b which permits a more automated performance of the third preferred embodiment of the method of the present invention for producing the "biological stent" in the urethral tissue a male patient suffering from a disease of the prostate which results in an enlarged prostate that causes the bore of the urethra be narrowed.

FIG. 3d shows that the structure of FIG. 3b may be modified to permit control of the microwave power output of microwave generator to be responsive to control signals fed back thereto in a manner generally similar to that shown in above-described FIG. 3c. The only functional difference between FIGS. 3c and 3d is that received power meter 312a of FIG. 3d replaces reflected power meter 306a of FIG. 3c in providing the second control signal to signal-controlled microwave generator 300a.

Further, it is apparent that in the implementation of the first preferred embodiment of the method of the present invention, radiometer 208 could be a signal-controlled temperature-measuring radiometer that feeds back a control signal to microwave generator 126 which causes the temperature measured by radiometer 208 to be used to control microwave generator 126 to lower the generated microwave energy (or, alternatively, turn generator 126 off) if it appears likely that the measured temperature is about to reach or, at least, has reached a maximum safe temperature.

Generalizing, it has been discovered that, in the use of a microwave balloon catheter in the treatment of urethral tissue, the value of a physical characteristic of the urethral tissue, such as its elasticity value or its microwave reflectivity value or its transmissivity value, none of which can be directly observed, noticeably changes in value when a "biological stent" is formed in the urethral tissue in response to the microwave heating of the urethral tissue to a safe but effective temperature (e.g., 45° C. to 50° C.). However, in accordance with the method of the present invention, the formation of the "biological stent" in the urethral tissue can be made manifest by a change in the directly observable value of an analog of the value this otherwise non-observable physical characteristic of the urethral tissue.

While the method of the present invention is primarily directed to the use of a microwave balloon catheter in the formation of a "biological stent" in the treatment of urethral tissue, this method is also applicable to the formation of a "biological stent" in the treatment of other types of tissue, such as blood-vessel tissue, for instance. Thus, the method of the present invention is useful in angioplasty treatment of the narrowed bore of a blood vessel.

Further, while the preferred embodiments of the present invention all employ microwave energy to heat urethral tissue to a temperature at which a "biological stent" is formed because microwave energy efficiently heats the urethral tissue underlying the surface urethral tissue, it is not essential that microwave energy be employed to heat the urethral tissue to the temperature at which a "biological stent" is formed. For instance, hot water could be used to provide the heating of the urethral tissue to the temperature at which a "biological stent" is formed.

What is claimed is:

1. In a method for treating a male patient suffering from a disease of the prostate which results in an enlarged prostate that causes the bore of the urethra be narrowed, said method comprising the steps of (1) longitudinally situating a deflated balloon of a microwave balloon catheter in said narrowed bore portion of the urethra of said patient that is in proximity to said patient's prostate, (2) inflating said balloon to an inflation pressure that applies sufficient squeezing pressure on urethral tissue of said narrowed bore portion to effect a certain amount of temporary widening of said narrowed bore portion as long as said squeezing pressure is maintained, and (3) employing a microwave generator having a microwave-transmitting antenna surrounded by said balloon to irradiate said temporarily widened bore portion of said urethral tissue with microwave energy to thereby effect the heating said portion of said urethral tissue; the improvement in said method for determining when said temporarily widened bore portion of said urethral tissue has been sufficiently heated to form a "biological stent" that is capable of maintaining said bore portion of said urethral tissue permanently widened after said irradiation has ceased, said balloon has been deflated and said squeezing pressure on said bore portion of said urethral tissue has been removed; said improvement comprising the further method step of:

(a) measuring an observable value of an analog of a value of a certain physical characteristic of said urethral tissue itself that permanently changes significantly in value from a first value to a second value when said "biological stent" in said urethral tissue is permanently formed in response to said urethral tissue having been sufficiently heated, thereby indicating when a "biological stent" in said urethral tissue has been permanently formed.

2. The method defined in claim 1, wherein said certain physical characteristic of said urethral tissue constitutes the elasticity of said urethral tissue, and wherein step (a) comprises the step of:

(b) continuously measuring the observable value of the inflation pressure inflating said balloon while said squeezing pressure on said urethral tissue is being maintained and while said portion of said urethral tissue is being irradiated with said microwave energy; whereby there is a noticeable observable drop in the measured value of the inflation pressure inflating said balloon when said "biological stent" is formed due to a noticeable drop in the value of back pressure exerted on said inflated balloon by said urethral tissue which is a consequence of a noticeable permanent drop in the value of the elasticity of said urethral tissue when said "biological stent" is formed.

3. The method defined in claim 2, further comprising the step of:

(c) continuously measuring the temperature of rectal tissue of said patient that is in proximity to said patient's prostate while said squeezing pressure on said urethral tissue is being maintained and while said portion of said urethral tissue is being irradiated with said microwave energy.

4. The method defined in claim 3, wherein step (c) comprises the step of:

(d) employing a temperature-measuring radiometer having a rectal probe for longitudinally situating a directional antenna in cooperative spatial relationship with said rectal tissue of said patient that is in proximity to said patient's prostate for receiving the intensity of temperature-indicative radiation emitted from said rectal tissue to thereby provide a continuous measurement of the temperature of said rectal tissue of said patient in accordance with the received intensity of temperature-indicative radiation emitted from said rectal tissue.

5. The method defined in claim 4, wherein step (d) comprises the step of:

(e) employing as said temperature-measuring radiometer a temperature-measuring radiometer that incorporates an alarm for signaling that said rectal tissue has been heated to a maximum safe temperature.

6. The method defined in claim 4, wherein step (d) comprises the step of:

(e) applying a control signal from said temperature-measuring radiometer to said microwave generator for limiting the microwave power from said microwave generator that irradiates said urethral tissue in accordance with the temperature measured by said temperature-measuring radiometer to thereby prevent said rectal tissue from being heated beyond a maximum safe temperature.

7. The method defined in claim 1, wherein said certain physical characteristic of said urethral tissue constitutes the reflectivity of said urethral tissue to said irradiating microwave energy, and wherein step (a) comprises the step of:

(b) continuously measuring an observable value of microwave power reflected from said urethral tissue while said squeezing pressure on said urethral tissue is being maintained and while said portion of said urethral tissue is being irradiated with said microwave energy; whereby there is a noticeable observable change in the measured value of the microwave power reflected from said urethral tissue when said "biological stent" is formed which is a consequence of a noticeable permanent change in the value of the reflectivity of said urethral tissue when said "biological stent" is formed.

8. The method defined in claim 7, wherein step (b) comprises the step of:

(c) employing a bi-directional coupler and a reflected power meter for forwarding said microwave energy from said microwave generator to said microwave-transmitting antenna through said bi-directional coupler and returning reflected microwave energy received by said microwave-transmitting antenna to said reflected power meter through said bi-directional coupler;

whereby the microwave power reflected from said urethral tissue is continuously measured by said reflected power meter.

9. The method defined in claim 8, further comprising the step of:

(d) employing a transmitted power meter for continuously measuring the transmitted microwave power of said microwave energy from said microwave generator being forwarded from said microwave generator to said microwave-transmitting antenna through said bi-directional coupler.

10. The method defined in claim 9, wherein said microwave generator is a signal-controlled microwave generator including logic means responsive to control signals applied thereto, and wherein said method further comprises the steps of:

(e) continuously feeding back from said transmitted power meter the current measurement of said transmitted microwave power as a first control signal to said signal-controlled microwave generator;

(f) continuously feeding back from said reflected power meter the current measurement of said reflected microwave power as a second control signal to said signal-controlled microwave generator; and (g) causing the transmitted microwave power output from said signal-controlled microwave generator to be turned off in response to a noticeable change in the value of the ratio of the current measurement of said transmitted microwave power to the current measurement of said reflected microwave power.

11. The method defined in claim 10, further comprising the steps of:

(h) employing a temperature-measuring radiometer having a rectal probe for longitudinally situating a directional antenna in cooperative spatial relationship with said rectal tissue of said patient that is in proximity to said patient's prostate for receiving the intensity of temperature-indicative radiation emitted from said rectal tissue to thereby provide a continuous measurement of the temperature of said rectal tissue of said patient in accordance with the received intensity of temperature-indicative radiation emitted from said rectal tissue; and applying a third control signal from said temperature-measuring radiometer to said signal-controlled microwave generator for limiting the microwave power from said signal-controlled microwave generator that irradiates said urethral tissue in accordance with the temperature measured by said temperature-measuring radiometer to thereby prevent said rectal tissue from being heated beyond a maximum safe temperature.

12. The method defined in claim 1, further comprising the step of:

(b) continuously measuring the temperature of rectal tissue of said patient that is in proximity to said patient's prostate while said squeezing pressure on said urethral tissue is being maintained and while said portion of said urethral tissue is being irradiated with said microwave energy.

13. The method defined in claim 12, wherein step (b) comprises the step of:

(c) employing a temperature-measuring radiometer having a rectal probe for longitudinally situating a directional antenna in cooperative spatial relationship with said rectal tissue of said patient that is in proximity to said patient's prostate for receiving the intensity of temperature-indicative radiation emitted from said rectal tissue to thereby provide a continuous measurement of the temperature of said rectal tissue of said patient in accordance with the received intensity of temperature-indicative radiation emitted from said rectal tissue.

14. The method defined in claim 13, wherein step (c) comprises the step of:

(k) employing a temperature-measuring radiometer incorporating an alarm for signaling that said rectal tissue has been heated to a maximum safe temperature.

15. The method defined in claim 13, wherein said certain physical characteristic of said urethral tissue constitutes the transmissivity of said urethral tissue to said irradiating microwave energy, and wherein step (a) comprises the step of:

(d) continuously measuring an observable value of that microwave power transmitted from said microwave-transmitting antenna which is received by said directional antenna while said squeezing pressure on said urethral tissue is being maintained and while said portion of said urethral tissue is being irradiated with said microwave energy;

whereby there is a noticeable observable change in the measured value of the microwave power transmitted from said microwave-transmitting antenna that is received by said directional antenna when said "biological stent" is formed which is a consequence of a noticeable permanent change in the value of the transmissivity of said urethral tissue when said "biological stent" is formed.

16. The method defined in claim 15, wherein step (d) comprises the step of:

(e) employing a microwave power distributor to distribute the microwave power transmitted from said microwave-transmitting antenna that is received by said directional antenna to a received power meter and to distribute the intensity of temperature-indicative radiation emitted from said rectal tissue to said temperature-measuring radiometer.

17. The method defined in claim 16, further comprising the step of:

(f) employing a transmitted power meter for continuously measuring the transmitted microwave power of said microwave energy from said microwave generator being forwarded from said microwave generator to said microwave-transmitting antenna.

18. The method defined in claim 17, wherein said microwave generator is a signal-controlled microwave generator including logic means responsive to control signals applied thereto, and wherein said method further comprises the steps of:

(g) continuously feeding back from said transmitted power meter the current measurement of said transmitted microwave power as a first control signal to said signal-controlled microwave generator;

(h) continuously feeding back from said received power meter the current measurement of said received microwave power as a second control signal to said signal-controlled microwave generator;

(i) continuously feeding back from said temperature-measuring radiometer meter the current measurement of temperature as a third control signal to said signal-controlled microwave generator; and (j) causing the transmitted microwave power output from said signal-controlled microwave generator to be turned off in response to a noticeable change in the value of the ratio of the current measurement of said transmitted microwave power to the current measurement of said received microwave power and for limiting the microwave power from said signal-controlled microwave generator that irradiates said urethral tissue in accordance with the value of the current measurement of said temperature to prevent said rectal tissue from being heated beyond a maximum safe temperature.

19. The method defined in claim 1, wherein step (2) comprises the step of:

(b) inflating said balloon, with a fluid material exhibiting a low loss factor to irradiating microwave energy relative to the loss factor of urethral tissue, to apply sufficient squeezing pressure on urethral tissue of said narrowed bore portion to effect a certain amount of temporary widening of said narrowed bore portion as long as said squeezing pressure is maintained.

20. The method defined in claim 19, wherein said fluid material exhibiting a low loss factor to irradiating microwave energy relative to the loss factor of urethral tissue is air.

21. The method defined in claim 1, comprising the further steps of:

(b) after said balloon has been deflated and said squeezing pressure on said bore portion of said urethral tissue has been removed, reinflating said balloon with a metered liquid only to a point at which a measured pressure of said metered liquid reinflating said balloon just starts to rise;

whereby the amount of said metered liquid reinflating said balloon at said point is a measure of the volume of said permanently-widened bore portion of said urethral tissue.

22. In a method for treating a narrowed bore portion of an orifice or vessel of a patient, said method comprising the steps of (1) longitudinally situating a deflated balloon of a balloon catheter in said narrowed bore portion of said orifice or vessel of said patient, (2) inflating said balloon to an inflation pressure that applies sufficient squeezing pressure on tissue of said narrowed bore portion of said orifice or vessel to effect a certain amount of temporary widening of said narrowed bore portion of said orifice or vessel as long as said squeezing pressure is maintained, and (3) heating said tissue of said temporarily widened bore portion of said orifice or vessel; the improvement in said method for determining when the tissue of said temporarily widened bore portion of said orifice or vessel has been sufficiently heated to form a "biological stent" that is capable of maintaining said tissue of said bore portion of said orifice or vessel permanently widened after said irradiation has ceased, said balloon has been deflated and said squeezing pressure on said tissue of said bore portion of said orifice or vessel has been removed; said improvement comprising the further method step of:

(a) measuring an observable value of an analog of a value of a certain physical characteristic of said tissue of said narrowed bore portion of said orifice or vessel itself that permanently changes significantly in value from a first value to a second value when said "biological stent" in said tissue of said narrowed bore portion of said orifice or vessel is permanently formed in response to said orifice or vessel tissue having been sufficiently heated, thereby indicating when a "biological stent" in said tissue of said narrowed bore portion of said orifice or vessel has been permanently formed.

23. The method defined in claim 22, wherein said physical characteristic of said orifice or vessel tissue constitutes the elasticity of said orifice or vessel tissue, and wherein step (a) comprises the step of:

(b) continuously measuring the observable value of the inflation pressure inflating said balloon while said squeezing pressure on said orifice or vessel tissue is being maintained and while said portion of said orifice or vessel tissue is being irradiated with said microwave energy;

whereby there is a noticeable observable drop in the measured value of the inflation pressure inflating said balloon when said "biological stent" is formed due to a noticeable drop in the value of back pressure exerted on said inflated balloon by said orifice or vessel tissue which is a consequence of a noticeable permanent drop in the value of the elasticity of said orifice or vessel tissue when said "biological stent" is formed.

24. The method defined in claim 22, wherein step (3) comprises the step of:

(b) employing a microwave generator having a microwave-transmitting antenna surrounded by said balloon to irradiate said temporarily widened bore portion of said orifice or vessel tissue with microwave energy to thereby effect said heating of said portion of said orifice or vessel tissue.

25. The method defined in claim 24, wherein said physical characteristic of said orifice or vessel tissue constitutes the reflectivity of said orifice or vessel tissue to said irradiating microwave energy, and wherein step (a) comprises the step:

(b) continuously measuring the observable value of microwave power reflected from said irradiated tissue of said orifice or vessel and fed back through a bi-directional coupler to a reflected power meter while said squeezing pressure on said orifice or vessel tissue is being maintained and while said portion of said orifice or vessel tissue is being irradiated with said microwave energy;

whereby there is a noticeable observable drop in the measured value of microwave power reflected from said irradiated tissue of said orifice or vessel when said "biological stent" is formed which is a consequence of a noticeable permanent drop in the value of the reflectivity of said orifice or vessel tissue when said "biological stent" is formed.

26. The method defined in claim 24, wherein said physical characteristic of said orifice or vessel tissue constitutes the transmissivity of said orifice or vessel tissue to said irradiating microwave energy, and wherein step (a) comprises the step:

(b) continuously measuring the observable value of microwave power transmitted through said irradiated tissue of said orifice or vessel and received by a microwave-receiving antenna coupled to a received power meter while said squeezing pressure on said orifice or vessel tissue is being maintained and while said portion of said orifice or vessel tissue is being irradiated with said microwave energy;

whereby there is a noticeable observable drop in the measured value of microwave power transmitted through said irradiated tissue of said orifice or vessel and received by said microwave-receiving antenna coupled to said received power meter when said "biological stent" is formed which is a consequence of a noticeable permanent drop in the value of the transmissivity of said orifice or vessel tissue when said "biological stent" is formed.

* * * * *